United States Patent [19]

Robison

[11] Patent Number: 4,749,652

[45] Date of Patent: Jun. 7, 1988

[54] LACTIC ACID PROCESS

[75] Inventor: Peter D. Robison, Poughkeepsie, N.Y.

[73] Assignee: Texaco Inc., White Plains, N.Y.

[21] Appl. No.: 766,479

[22] Filed: Aug. 19, 1985

[51] Int. Cl.$^4$ .......................... C12P 7/56; C12N 1/36; C12R 1/225

[52] U.S. Cl. ................................. 435/139; 435/245; 435/853

[58] Field of Search .............. 435/139, 253, 245, 853

[56] References Cited

U.S. PATENT DOCUMENTS 4,349,569 9/1982 Peer ................................ 435/245 X
4,432,998 2/1984 Peer ................................ 435/843 X

FOREIGN PATENT DOCUMENTS 1039964 9/1983 U.S.S.R. ............................. 435/139

OTHER PUBLICATIONS

Golubchina, R. et al., Chem. Abstr. 101: 126554p, 1984.
Kalinina et al., Chem. Abstr. 88: 47375h, 1978.

Primary Examiner—Elizabeth Weimar
Attorney, Agent, or Firm—Robert A. Kulason; James J. O'Loughlin

[57] ABSTRACT

A variant strain of the organism *Lactobacillus delbrueckii*, accession number ATCC 53197, is provided as well as an improved process for the preparation of lactic acid by the fermentation of carbohydrates using the method strain of *Lactobacillus delbrueckii*.

4 Claims, No Drawings

LACTIC ACID PROCESS

BACKGROUND OF THE INVENTION

This invention relates to an improved process for the manufacture of lactic acid by the fermentation of a carbohydrate in an aqueous nutrient medium by the microorganism *Lactobacillus delbrueckii*.

It is known to produce lactic acid by the fermentation of carbohydrates using *Lactobacillus delbrueckii*. However, the effectiveness of *Lactobacillus delbrueckii* for producing lactic acid is significantly inhibited by the lactic acid product. The result is that as the concentration of the lactic acid increases during the fermentation process, the production of lactic acid is substantially reduced.

It is an object of this invention to provide a process in which the production of lactic acid is substantially improved by employing a strain of *Lactobacillus delbrueckii* which is resistant to lactic acid inhibition.

SUMMARY OF THE INVENTION

In the microbiological method of preparing lactic acid by converting carbohydrates to lactic acid by growing *Lactobacillus delbrueckii* in a suitable nutrient medium, an improvement has been developed which comprises using a variant strain of *Lactobacillus delbrueckii*, accession number ATCC 53197, in a fermentation at a pH from about 6.3 to 6.5 and a temperature in the range of 40° to 50° C.

The variant strain of the microorganism *Lactobacillus delbrueckii*, accession number ATCC 53197, can be prepared and the culture isolated by a method which comprises carrying out a series of fermentation cycles at about 45° C. starting with a wild strain of *Lactobacillus delbrueckii*, Strain NRRL-B445 (obtained from the Northern Regional Research Laboratories in Peoria, Ill.), which grows in an aqueous nutrient medium containing assimilable sources of carbon, nitrogen and inorganic substances at a pH of about 6.3 to 6.5.

Each fermentation cycle consists of a series of fermentation steps in which the prescribed culture is grown in the presence of a nutrient medium that has been modified by the addition of lactic acid to the medium with increasing amounts of lactic acid being employed in the fermentation steps. The amount of lactic acid present in the nutrient medium in each fermentation step ranges from about 5 to 10 volume percent of lactic acid. In general, a number of fermentation cycles are employed following which a strain of *Lactobacillus delbrueckii*, accession number ATCC 53197, is recovered which is effective for producing at least 14 weight percent of lactic acid from a medium containing 20 weight percent of a carbohydrate, such as glucose.

The fermentation temperatures for making the prescribed variant strain of *Lactobacillus delbrueckii* can range from about 40° to 50° C. with the preferred temperature being about 45° C.

Typical carbohydrates which can be converted to lactic acid by fermentation in the presence of the variant strain of *Lactobacillus delbrueckii*, accession number ATCC 53197, include glucose, maltose, sucrose and fructose.

EXAMPLE

In this example, a comparison is made between the previously known *Lactobacillus delbrueckii* from strain NRRLB445 (obtained from the Northern Research Laboratories in Peoria, Ill.) and the variant strain of *Lactobacillus delbrueckii*, accession number ATCC 53197.

The variant strain of *Lactobacillus delbrueckii* was prepared in a medium that was modified to contain different concentrations of lactic acid in a series of fermentations leading to the production of the variant strain. The basic medium had the following composition:

Medium 10 g. glucose
10 g. tryptone
5 g. yeast extract
3 g. $K_2HPO_4$
0.2 g. cysteine
5 mls R Salts
1 ml Tween 80
distilled $H_2O$ to 1 liter

R Salts 11.5 g $MgSO_4.7H_2O$
0.68 g. $FeSO_4.7H_2O$
2.40 g. $MnSO_4.2H_2O$
distilled $H_2O$ to 100 mls The growth and selection of the variant strain was carried out in a one liter New Brunswick scientific fermentor using the above noted medium, a pH of about 6.3 and a temperature of 45° C. *Lactobacillus delbrueckii* NRRL-B445 was grown in a series of fermentations using increasing amounts of lactic acid. In the first fermentation cycle, the NRRL strain B445 was grown in a medium which had been modified to contain 5 volume percent of lactic acid. The organism obtained was transferred to a medium modified to contain 6 volume percent of lactic acid and the organism obtained in the second step transferred to a medium modified to contain 7 volume percent of lactic acid. The organism obtained from the third step was transferred into another fermentation medium modified to contain 7 volume percent of lactic acid. At the end of the fourth fermentation step in this cycle, the organisms were plated out and a single colony was isolated.

The isolate from the first fermentation cycle was transferred into a one liter fermentor and regrown in a medium in a series of fermentation steps containing lactic acid. The second fermentation cycle consisted of five fermentation steps containing successively five, six, six, seven and seven volume percent of lactic acid. At the end of the second cycle of five fermentation steps, a single colony was isolated.

The isolate from the second fermentation cycle was transferred to a one liter fermentor and another series of fermentations were conducted in a third fermentation cycle. In this cycle, the organisms were grown in a medium containing successively seven, eight, nine and ten percent of lactic acid after which a single colony was isolated.

The isolate recovered from the third fermentation cycle was again transferred to a one liter fermentor in a medium modified by the addition of lactic acid. In this cycle, the organism was grown in successive fermentation steps containing respectively eight, eight, nine, ten and ten volume percent of lactic acid. The isolate recovered at the end of the fourth fermentation cycle was the novel variant strain of *Lactobacillus delbrueckii*, Accession Number ATCC 53197.

The effectiveness of the new strain of *Lactobacillus delbrueckii*, Accession Number ATCC 53197 as compared to the known strain of *Lactobacillus delbrueckii*, NRRL B-445, was compared by introducing each organism to separate fermentors containing a medium with 20% glucose. The resuts of the tests obtained after 7–9 days are set forth in Table I:

TABLE I

|  | % Lactic Acid | % Yield | % Glucose | % Conversion |
|---|---|---|---|---|
| NRRL B-445 Isolate | 12.3 | 96 | 4.5 | 74 |
| ATCC 53197 (avg. of two runs) | 14.05 | 93.5 | 1.7 | 89 |

The foregoing data show that the variant strain of *Lactobacillus delbrueckii*, accession number ATCC 53197, provides a substantial increase in the conversion of the carbohydrate in the media with a conversion $$\left( \frac{g.\ glucose\ fermented}{g.\ original\ glucose} \right)$$

higher for the variant and a higher total amount of lactic acid produced.

What is claimed is:

1. In a process for preparing lactic acid which comprises fermenting a carbohydrate in a aqueous nutrient medium at a temperature ranging from about 40° to 50° C., and a pH ranging from about 6.3 to 6.5, said carbohydrate comprising at least 20 weight percent of said nutrient medium with a novel strain of *Lactobacillus delbrueckii* ATCC 53197, said strain of *Lactobacillus delbrueckii*, ATCC 53197 being prepared by subjecting a wild strain of *Lactobacillus delbrueckii* NRRL-B445 to at least four serial fermentations conducted in a nutrient medium containing lactic acid, said serial fermentations being conducted at increasing concentrations of lactic acid ranging from 5 to 7, 5 to 7, 7 to 10 and 8 to 10 volumes percent of lactic acid respectively, and recovering said novel strain of *Lactobacillus delbrueckii* ATCC 53197.

2. A method according to claim 1 in which said process is effective for producing at least 14 weight percent of lactic acid.

3. A process according to claim 1 in which said carbohydrate is selected from the group consisting of glucose, maltose, sucrose and fructose.

4. A process according to claim 1 in which said serial fermentations of said wild strain of *Lactobacillus delbrueckii* NRRL-B445 are conducted at a pH ranging from about 6.3 to 6.5.

* * * * *